US00PP08727P

United States Patent [19]

Schumann

[11] Patent Number: Plant 8,727

[45] Date of Patent: May 10, 1994

[54] GERANIUM PLANT NAMED FISDIA

[75] Inventor: Ingeborg Schumann, Albstadt, Fed. Rep. of Germany

[73] Assignee: Florfis/AC, Binningen, Switzerland

[21] Appl. No.: 94,327

[22] Filed: Jul. 21, 1993

[51] Int. Cl.[5] ..... A01H 5/00
[52] U.S. Cl. ..... Plt./87.12
[58] Field of Search ..... Plt. 87.12

*Primary Examiner*—James R. Feyrer
*Attorney, Agent, or Firm*—Foley & Lardner

[57] ABSTRACT

A new and distinct cultivar of geranium named Fisdia, particularly characterized by the combined features of vermillion red flower color, semi-double flower type, dark green foliage, medium growth habit and comparatively early spring flower response.

1 Drawing Sheet

The present invention comprises a new and distinct cultivar of geranium, botanically known as *Pelargonium zonale* l'hert, and hereinafter referred to by the cultivar name Fisdia.

Fisdia is a product of planned breeding program which had the objective of creating new geranium cultivars with bright red flower color, dark foliage and relatively early flower response.

Fisdia was originated from a hybridization made by the inventor Ingeborg Schumann in a controlled breeding program in Galdar, Gran Canaria, Spain in 1987. The female parent was the patented variety Mars (U.S. Plant Pat. No. 5,372), characterized by orange red semi-double flowers, medium green foliage, medium plant habit and very good branching ability. The male parent of Fisdia was an unnamed hybrid produced by crossing an inbred line of Alex (also known by varietal name Kim in the United States) and a tetraploid line of Stadt Bern. Alex is characterized by red flower color, and medium green foliage without zonation. Stadt Bern has single orange red flowers and dark foliage with very strong zonation.

Fisdia was discovered and selected as one flowering plant within the progeny of the stated cross by Ingeborg Schumann in 1988 in a controlled environment in Galdar, Gran Canaria, Spain.

The fist act of asexual reproduction of Fisdia was accomplished when vegetative cuttings were taken from the initial selection in February 1989 in a controlled environment in Galdar, Gran Canaria, Spain, by, or under the supervision of, Ingeborg Schumann.

Horticultural examination of plants grown from these cuttings initiated in May 1989, and containing thereafter, has demonstrated that the combination of characteristics as herein disclosed for Fisdia are firmly fixed and are retained through successive generations of asexual reproduction.

Fisdia has not been observed under all possible environmental conditions. The phenotype may vary significantly with variations in environment such as temperature, light intensity and day length without, however, any variation in genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristic of Fisdia, which in combination distinguish this geranium as a new and distinct cultivar:

1. Dutch vermillion red flower color
2. Semi-double round flower type
3. Large umbels
4. Dark green foliage
5. Comparatively early flower response, for a dark green cultivar Of the many commercial cultivars known to the present inventor, the most similar in comparison to Fisdia is the patented variety Tango, disclosed in Plant Pat. No. 5,933.

Reference is made to attached Chart A which compares certain characteristics of Fisdia to those same characteristics of Tango.

In general comparison to Tango, Fisdia has a mored red shade of flower color, less tendency to change color with maturity, stronger anthocyanin coloring of sepals, pedicels and peduncles, and a somewhat earlier spring flower response.

The accompanying color photographic drawing shows typical flower and foliage characteristics of Fisdia, with colors being as true as possible with illustrations of this type.

In the following description color references are made to The Royal Horticultural Society Colour Chart. The color values were determined indoors from plants grown in the greenhouse in May from plants grown indoors in Hillscheid, Federal Republic of Germany.

Classification:

*Botanical.*—A hybrid of the species *Pelargonium zonale* l'Hert.

*Commercial.*—Zonal geranium, cv., Fisdia.

INFLORESCENCE

A. Umbel:

*Shape.*—Semi-spherical to spherical.
*Average diameter.*—120 mm.
*Average depth.*—75 mm.
*Peduncle length.*—195 mm.
*Peduncle color.*—Green indoors, light red outdoors.
*Pedicel length.*—30 mm.
*Pedicel color.*—Light to dark red.
*Number of flowers per umbel.*—40–50.

B. Corolla:

*Average diameter.*—47 mm.
*Form.*—Semi-double.
*Number of petals.*—8–11.

*Number of petaloids.*—2–4.

*Color (general tonality from a distance of three meters).*—Vermillion red.

*Color of upper petals.*—43 A.

*Color of lower petals.*—43 A.

*Color of lower surface of petals.*—40 A.

*Color of sepals.*—Dark red.

*Number of sepals.*—5.

C. Bud:

*Shape.*—Elliptic

*Color (adaxial).*—Green, with anthocyanin at the base.

*Color (abaxial).*—Red.

D. Reproductive organs:

*Androecium.*—4–6 fertile anthers, white filaments, orange pollen.

*Gynoecium.*—5–6 lobed stigma, red style and stigma.

E. Spring flowering response period: In Hillscheid, Federal Republic of Germany, in 1993 plants had on average 1.4 flowers opened 11 weeks after planting of unrooted cuttings.

F. Outdoor flower production: The flower count in 1992 in Hillscheid, Federal Republic of Germany was between 35 and 40 flowers per plant for May through August observation period.

G. Durability: Good shatter resistance.

PLANT

A. Foliage:

*Form.*—Kidney-shaped.

*Margin.*—Bicrenated.

*Size of leaf.* 9–10 cm.

*Color of upper surface.*—Dark green, approximately 137A.

*Color of zonation.*—Darker green (weak, not always visible).

*Tolerance of botrytis.*—Average.

B. General appearance and form:

*Internode length.*—About 3 cm.

*Branching pattern.*—3.0 branches per week.

*Height (13 week old plants).*13 16 cm.

CHART A

| CHARACTERISTIC | FISDIA | ROSPEN |
|---|---|---|
| Flower color, upper petals | 43 A | 44A–45B |
| Change of color with maturity | Dark orange to brown | Rose red with a more bluish shade |
| Color of pedicels | Light to dark red | Green to light red |
| Spring flower response: number of flowers on 11 week old plants (average, 1991–93) | 1.13 | 0.9 |

I claim:

1. A new and distinct cultivar of geranium plant named Fisdia, as illustrated and described.

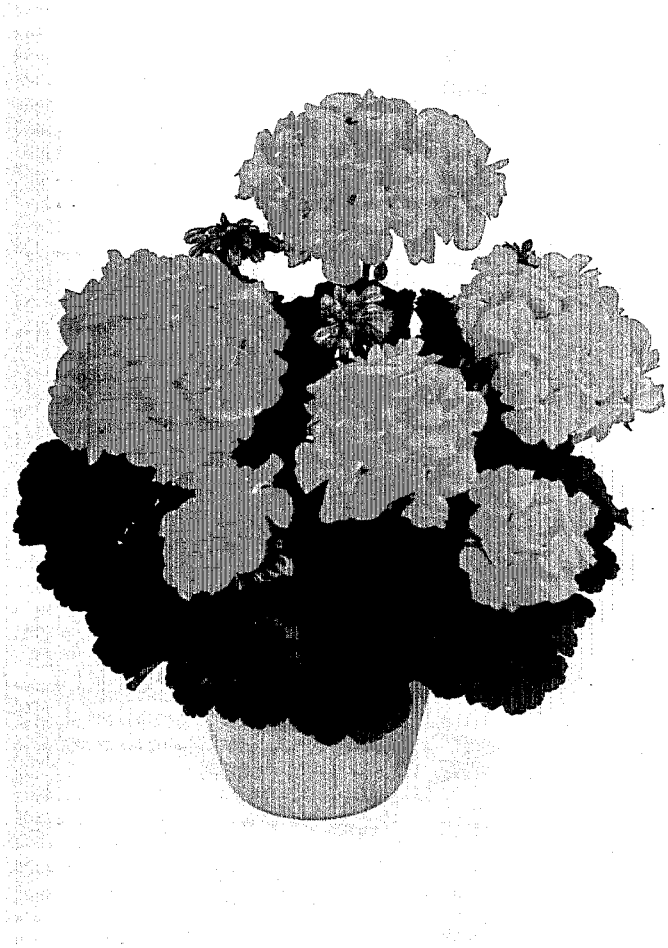

* * * * *